(12) United States Patent
Fuisz et al.

(10) Patent No.: US 8,992,950 B2
(45) Date of Patent: Mar. 31, 2015

(54) SOLID DOSAGE FORM THAT PROMOTES RELIABLE ORAL, ESOPHAGEAL AND GI TRANSIT

(71) Applicants: Richard C. Fuisz, Beverly Hills, CA (US); Joseph M. Fuisz, Surfside, FL (US)

(72) Inventors: Richard C. Fuisz, Beverly Hills, CA (US); Joseph M. Fuisz, Surfside, FL (US)

(*) Notice: Subject to any disclaimer, the term of this patent is extended or adjusted under 35 U.S.C. 154(b) by 0 days.

(21) Appl. No.: 13/759,138

(22) Filed: Feb. 5, 2013

(65) Prior Publication Data
US 2013/0149353 A1 Jun. 13, 2013

Related U.S. Application Data

(60) Division of application No. 13/079,285, filed on Apr. 4, 2011, now Pat. No. 8,383,135, which is a continuation-in-part of application No. 12/960,192, filed on Dec. 3, 2010, now abandoned.

(51) Int. Cl.

| | | |
|---|---|---|
| A61B 1/04 | (2006.01) | |
| A61J 3/07 | (2006.01) | |
| A61J 3/10 | (2006.01) | |
| A61K 9/20 | (2006.01) | |
| A61K 9/48 | (2006.01) | |
| A61K 31/192 | (2006.01) | |
| A61K 31/616 | (2006.01) | |

(52) U.S. Cl.
CPC .... *A61J 3/07* (2013.01); *A61J 3/10* (2013.01); *A61K 9/2072* (2013.01); *A61K 9/4808* (2013.01); *A61K 31/192* (2013.01); *A61K 31/616* (2013.01)
USPC ........................................................ 424/400

(58) Field of Classification Search
None
See application file for complete search history.

(56) References Cited

U.S. PATENT DOCUMENTS

| 4,167,558 A | 9/1979 | Sheth et al. |
| 4,258,027 A | 3/1981 | Ullman |

(Continued)

FOREIGN PATENT DOCUMENTS

| CH | 696 229 A5 | 2/2007 | |
| DE | 20 2008 011 931 U1 | 11/2008 | |
| WO | WO 2010/002033 | * 1/2010 | ............... A61K 9/20 |

OTHER PUBLICATIONS

International Search Report/Written Opinion, PCT/US2011/063027, Jul. 6, 2012.

(Continued)

*Primary Examiner* — Brian Gulledge
(74) *Attorney, Agent, or Firm* — Atonelli, Terry, Stout & Kraus, LLP.

(57) ABSTRACT

A solid dosage form designed to facilitate rapid and reliable oral, esophageal and GI transit has a surface area of the contact patch, i.e., the area of contact between the dosage form and the bodily surface reduced. The dosage form can be an asymmetric oral dosage unit containing a bioactive, the dosage unit being asymmetric with respect to a rotational axis perpendicular to a longitudinal axis of the dosage form, the rotational axis being located substantially at a mid point along the longitudinal axis. The dosage unit may have an outer surface ridged or dimpled or have at least one annular ring so as to reduce the contact patch of the dosage unit with a flat surface compared to non-ridged dosage unit of the same size and shape. The oral dosage unit can also have a spherical shape with or without ridges and/or dimples. Dies for forming these oral dosage units have, in a closed state, a cavity having a shape corresponding to the oral dosage unit.

8 Claims, 6 Drawing Sheets

(56) References Cited

U.S. PATENT DOCUMENTS

| | | |
|---|---|---|
| 5,074,426 A | 12/1991 | Goodhart et al. |
| 5,562,920 A * | 10/1996 | Demmer et al. .............. 424/464 |
| 5,756,124 A | 5/1998 | Patel et al. |
| 6,161,260 A | 12/2000 | Flewitt |
| 2005/0175709 A1 | 8/2005 | Baty, III et al. |
| 2007/0010709 A1* | 1/2007 | Reinschke ................... 600/116 |
| 2008/0226705 A1 | 9/2008 | Solters et al. |

OTHER PUBLICATIONS

Overgaard et al., Patient's Evaluation of Shape, Size and Colour of Solid Dosage Forms, Pharmacy World & Science, vol. 23, No. 5, 2001, pp. 185-188.

EP Search Report of Appln. No. 11845539.3 dated Apr. 28, 2014 in English.

* cited by examiner

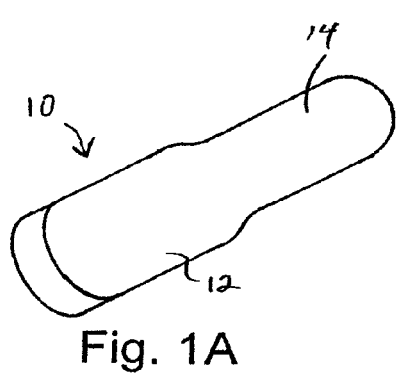
Fig. 1A
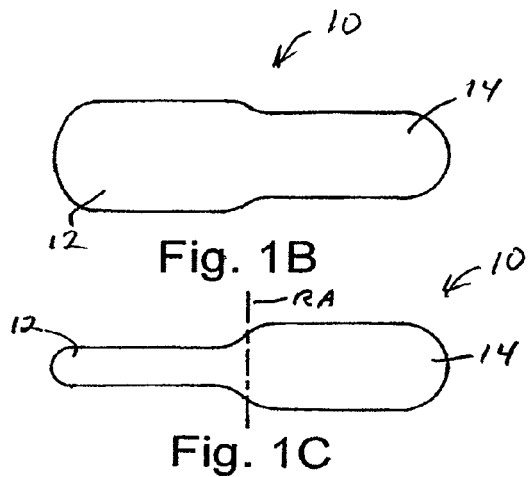
Fig. 1B
Fig. 1C
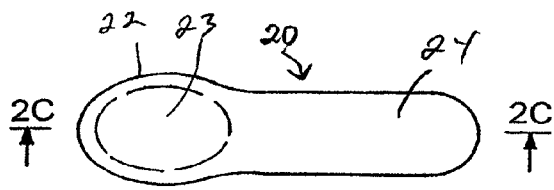
Fig. 2A
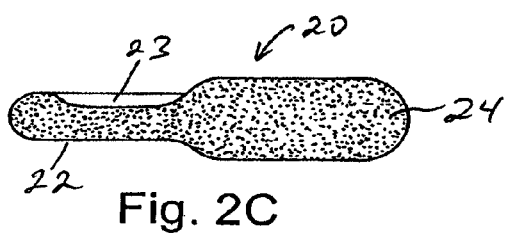
Fig. 2C
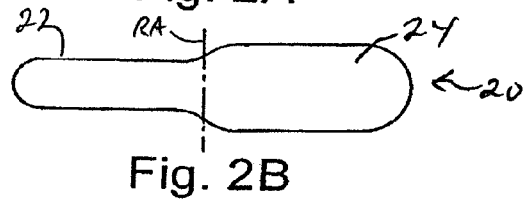
Fig. 2B
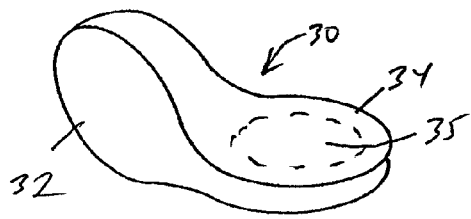
Fig. 3A
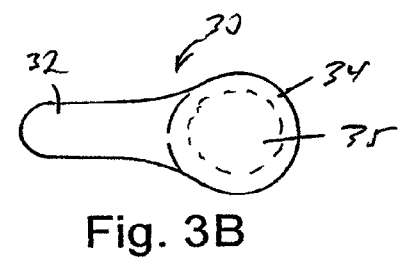
Fig. 3B
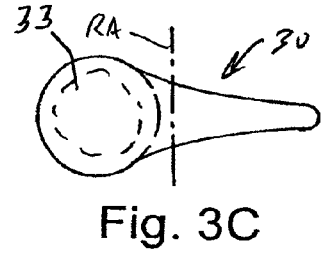
Fig. 3C

SOLID DOSAGE FORM THAT PROMOTES RELIABLE ORAL, ESOPHAGEAL AND GI TRANSIT

CROSS-REFERENCE TO RELATED APPLICATION

This application is a divisional of application Ser. No. 13/079,285, filed Apr. 4, 2011, which is a continuation-in-part of application Ser. No. 12/960,192, filed Dec. 3, 2010, the contents of each of which are incorporated herein by reference.

BACKGROUND

The swallowing of oral medications has long been understood to be problematic for large segments of the population. As many as one third of the United States patient population perceives difficulty in swallowing tablets, capsules, caplets and liquigels. Such difficulties are particularly acute for dysphagics, cancer patents, the elderly, children and other groups (for a good primer on causes of swallowing difficulties, see the Mayo Clinic's online treatment of the issue.

The issue of difficulty with swallowing oral medications involves several problems. One problematic group is the case of a physiologically "normal" patient who perceives difficulties or discomfort in swallowing solid oral medications. Such patients commonly fail to take their medications in a compliant manner. They may not take their medications when recommended, if at all. Frequently, they will crush their tablets, which may defeat time release systems or otherwise adversely alter the desired pharmacokinetic performance of the drug.

The most immediately severe swallowing problem is Actual Esophageal Transit Failure (AETF)—where the tablet actually becomes lodged or sticks in the esophagus. Such failure is generally understood to occur where transit takes thirty seconds or greater but in many cases the transit failure can be total until dissolution. Apart from the failure to deliver the intended medication, many classes of drugs are corrosive to the esophagus. While bisphosphonates, like Fosamax® are commonly understood by practitioners to pose a threat to the esophagus, the medical literature demonstrates that there many classes of drugs that pose a danger—over seventy drugs have been reported to cause esophageal disorders (including inter alia, anti bacterials like doxycycline, tetracycline, clindamycin, etc (see D. Jaspersen, "Drug-induced oesphageal disorders: pathogenesis, incidence, prevention and management," Drug Saf. 2000; March; 22(3): 237-49)). The typical practitioner is not always familiar with this literature, or simply does not have the knowledge or tools to remedy the issue.

A further problem is posed by the effect of delayed esophageal transit on the timing of peak drug concentration—effective blood levels can be materially delayed by common place transit failure. In a study of twenty patients awaiting cardiac catheterization, 11 patients took an acetaminophen tablet while supine. Transit was delayed in ten of these eleven subjects. The authors observed: "when there was delayed esophageal transit of tablets, the initial absorption of acetaminophen (measured as AUC over the first 60 min) was lower than that after normal esophageal transit of tablets. The peak plasma acetaminophen concentration was also lower and occurred 90 min later when transit was delayed. These kinetic changes decrease the effectiveness of acetaminophen as an analgesic." See K. S. Channer and C J Roberts, "Effect of Delayed Esophageal Transit on Acetaminophen Absorption" Clinical Pharmacology and Therapeutics 37, 72-76 (1 Jan. 1985).

To date, there have been two primary attempts to address this issue. The first effort has been the invention of rapidly dissolving dosage forms that dissolve in the mouth prior to esophageal transit, most prominently quick dissolve tablets. Various manufacturing methods have been taught and commercialized, including, the Zydis® freeze dried tablet, CIMA's Orasolv® effervescent tablet (now owned by Cephalon), Fuisz Technologies' Flashdose® shearform matrix (invented principally by one of the inventors hereof, Richard C. Fuisz, M.D.), and others. Additionally, other quick dissolving dosage forms have been taught, such as thin film (see the following issued patents on thin film by the current inventors: Fuisz et al. U.S. Pat. Nos. 7,425,292, 7,500,984, 7,666,332, 7,824,588 and 7,897,080)). Sheet and slab dosage forms are another alternative (see e.g. Fuisz US 20100247612A1). Transdermal, vaginal, intra-nasal, buccal, inhalation, intraocular and other systems bypass swallowing entirely. In practice, not all drugs will be suitable for such alternative delivery forms as is manifest in the market share of drug consumption by delivery site.

The second primary attempt to address swallowing difficulties of solid dosage forms has involved the introduction of a superior liquid, to either replace or in some cases augment water during the administration. For example one of the present inventors teaches a liquid with enhanced rheological properties that replaces water during solid dosage form administration and eases esophageal transit by enveloping the solid dosage form in boundary layers of liquid (see one of the current inventor's Fuisz U.S. Pat. No. 6,337,083; see also, Baichwal et al. U.S. Pat. No. 5,670,169; Unger U.S. Pat. No. 6,134,276; Robertson US2007/068012; Fukui C A 2 538 755; and Dairiku et al. EP 0 0873 749). However, the commercial reality has been that companies have been slow to adopt the use of enhanced liquids with the additional distribution and costs issues implied thereby. The solid dosage form—administered with water—remains the gold standard of convenience and cost containment for the administration of most drugs.

The mechanics of esophageal transit for a conventional solid dosage form (e.g. a tablet) have been lightly studied but with provocative implications. For example, a study at the University of Berlin demonstrates that, when administering tablets with water, the volume of water and the position (erect being best) of the patent are key drivers: in the upright position, 45% of capsules were trapped in the oesophagus at a swallowing volume of 5 mL, 7% at 25 mL and 0% at 50 mL. In the supine position, the retention rate was 54% at 5 mL, 28% at 25 mL and 4% at 50 mL (See "Oesophageal transport of solid dosage forms depends on body position, swallowing volume and pharyngeal propulsion velocity," E. Osmanoglou et al, Neurogastroenterol Motil (2004) 16, 547-556; See also, "Measurement of the Esophageal Transit Time Using a Magnetic Market" Cordova-Fraga et al, Eighth Mexican Symposium On Medical Physics). Thus, the primary finding of Osmanoglu et al. is that upright administration with a high volume of liquid promotes reliable transit. This finding is incorporated in the instructions that accompany bisphosphonates like Fosamax® and Actonel® wherein the patient is instructed to take the tablet with a large amount of water and then remain standing for one hour afterwards. Of course, upright administration with large volumes of water is not practical for many patient populations, and supine or semi supine administration is the reality for many care situations.

Additionally, as the population ages, the compliant use of specific volumes of water for swallowing becomes more problematic.

There is a limited body of literature that addresses the relative ease of swallowing of various, conventional solid dosage forms as compared with one another. See Hey et al ("Oesophageal transit of six commonly used tablets and capsules" British Medical Journal Volume 285, Dec. 11, 1982) (concluding that "small tablets are swallowed most easily," and large tablets should be "oval and not round," and "capsules of a high density are easier to swallow than lighter ones."); Drake et al. ("Monitoring esophageal transit of wax-polished Alendronate in healthy postmenopausal women: a new technique for the study of pill transit time" Current Therapeutic Research, 2002 vol. 62 n 2, pp 103-109) (concluding that "oval wax-polished alendronate tablets pass through the esophagus rapidly"); Perkins et al ("Impaired oesophageal transit of capsule versus tablet formulations in the elderly" Gut. 1994 October 35 (10): 1363-1367) (concluding "gelatin capsules showed a clear tendency to remain within the oesphagus of healthy elderly volunteers, while similar sized enteric tablets did not."); Channer et al ("The effect of size and shape of tablets on their esophageal transit" J Clin Pharmacol. 1986 February; 26(2): 141-6) (concluding "large oval tablets had significantly shorter times than did large round tablets" and "retention of large oval and round tablets in the esophagus occurred in 20% of patients after swallowing while in the standing position. No medium sized tablet was retained, but in 4% of patients, a small tablet remained in the esophagus."); Perkins et al. ("Esophageal transit and in vivo disintegration of branded risedronate sodium tablets and two generic formulations of alendronic acid tablets" Clinical Therapeutics, Volume 30, Issue 5, May 2008 pp 834-844) ("the branded risedronate tablet has a significantly faster transit time than the 2 generic formulations of alendronate tested."); and Perkins et al. ("The use of scintigraphy to demonstrate the rapid esophageal transit of the oval film-coated placebo risedronate tablet compared to a round uncoated placebo tablet when administered with minimal volumes of water" Int J. Pharm. 2001 Jul. 17; 222(2): 295-303) (observing "no stasis was observed for the oval film coated placebo risedronate tablet"). Cooker US 2004/0101540 A1 posits that oral dosage forms should be more dense: "it is buoyancy that resists the swallowing process." (Crooker paragraph 43). Crooker teaches a solid dosage form that will totally submerge or partially submerge in water with an intended vertical positioning alignment. Crooker lacks any in vitro (or in vivo) testing methods, and in fact, we show the opposite to be the case.

However, a review of the foregoing literature demonstrates that it is essentially an ad hoc comparison of one existing solid dosage form's performance with another. There is no real inquiry into first principles of tablet design, nor a suggestion to do so, nor any substantive conclusions concerning the same. Even the question of tablet buoyancy is lightly touched upon and incorrectly at that. For representative samples of the patent art on tableting, see Snowden US 2006/0246136 A1 (Systems, Methods, Apparatuses for Manufacturing Dosage Forms), Berner et al U.S. Pat. No. 6,488,962 (Tablet shapes to enhance gastric retention of swellable controlled-release), Hampton et al. U.S. Pat. No. 5,213,738 (Method for making a capsule-shaped tablet) Lowby U.S. Pat. No. 3,166,476 (Powder Based Tablets).

Despite a lack of understanding of tablet design and swallowing, potential damage from esophageal failure is understood in the scientific literature, if not by the broader medical community. See Jaspersen (cited above), Eckstein et al. ("Iron tablets cause histopathologically distinctive lesions in mucosal biopsies of the stomach and esophagus" Pathology 1996 May 28(2): 142-5); Abid et al (Pill-induced esophageal injury: endoscopic features and clinical outcomes" Endoscopy, 2005 August 27(8): 740-4); Maskins et al "Gastrointestinal side effects of drugs" Expert Opin Drug Saf. 2003 July 2(4): 421-9), etc.

Each of the foregoing references is specifically incorporated as if fully stated herein, together with all references.

SUMMARY

The present inventors contemplate that substantial benefit to the public health could be conferred by the invention of solid dosage forms that are expressly designed to facilitate rapid and reliable oral, esophageal and GI transit.

We believe that the prior art was not directed at the proper understanding of the role of the contact patch on the mucosal surface and its relation to retarding sticking and the summation of these on the ease of transit starting with the oral cavity and tongue and following on down to the GI tract.

Thus, the present invention relates to a solid dosage form designed to facilitate rapid and reliable oral, esophageal and GI transit where the surface area of the contact patch, i.e., the area of contact between the dosage form and the bodily surface, is reduced. The dosage form can be an asymmetric oral dosage unit containing a bioactive, the dosage unit being asymmetric with respect to a rotational axis perpendicular to a longitudinal axis of the dosage form, the rotational axis being located substantially at a mid point along the longitudinal axis. The dosage unit may have an outer surface ridged or dimpled or have at least one annular ring so as to reduce the contact patch of the dosage unit with a flat surface compared to non-ridged dosage unit (or dosage unit lacking an annular ring) of the same size and shape. The oral dosage unit can also have a spherical shape.

Dies for forming these oral dosage units have, in a closed state, a cavity having a shape corresponding to the oral dosage unit.

BRIEF DESCRIPTION OF THE DRAWINGS

FIG. 1A is a perspective view of one embodiment of an oral dosage unit of the present invention;

FIG. 1B is a top plan view thereof; and

FIG. 1C is a front elevation view thereof (looking from an angle 90° from that of FIG. 1B).

FIG. 2A is a top plan view of another embodiment of an oral dosage unit of the present invention;

FIG. 2B is a front elevation view thereof (looking from an angle 90° from that of FIG. 2A); and FIG. 2C is a cross-sectional view along lines 2C-2C of FIG. 2A.

FIG. 3A is a perspective view of still another embodiment of an oral dosage unit of the present invention;

FIG. 3B is a top plan view thereof; and

FIG. 3C is a front elevation view thereof (looking from an angle 90° from that of FIG. 3B).

DISCLOSURE OF THE INVENTION

Figure 4A:
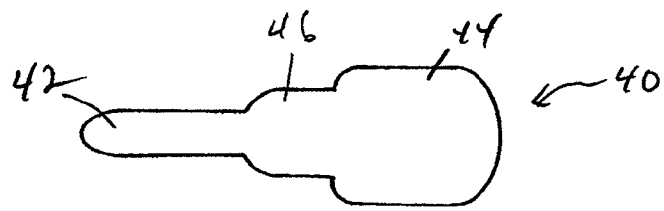
FIG. 4A is a top plan view of yet another embodiment an oral dosage unit of the present invention.

It is an object of the present invention to comprise and manufacture a solid dosage form designed to promote more rapid and more reliable oral, esophageal and GI transit, as well as to provide some non limiting illustrated die information.

The design of a tablet (or capsule or caplet or liquigel or any solid dosage form) ideally should address the most important factor in a dosage unit being difficult to transit—and that is sticking. Sticking is directly related of the size of the surface area of the contact patch—i.e., the area of contact between the dosage form and the bodily surface. Now in Newtonian physics we are taught that the area of contact does not matter in static friction. This does not apply however in the case of solid dosage form because the moist environment of the GI tract promotes an adhesion between the mucosa and the typical dosage unit surface. The propensity to adhere can be greatly reduced by minimizing the surface area where adhesion can occur. Reducing adhesion promotes successful transit. One way that we accomplish this is through the asymmetrical dosage since this results in a substantial reduction in the contact patch when compared to the symmetrical dosage units we are all accustomed to. An asymmetric dosage unit will tend to minimize the contact patch. An additional approach involves a low order symmetrical design. An alternative approach is to employ dimples and/or ridges and/or an annulus or ring on a conventional design or in the aforementioned asymmetric unit in order to reduce the contact surface area. Yet another method is to use a sphere or perfectly round ball type dosage unit with or without dimples and/or ridges.

Typically, drugs are evaluated by the FDA for their ability to be safe and effective. Clearly in order to do this they must traverse the esophagus and the GI tract, including but not limited to, the mouth. Since the population of much of the world is aging demographically, many factors, such as but not limited to, nutrition, mobility, mental acuity, being bedridden etc. complicate the swallowing and transit of the heretofore known solid dosage units, which had little or no consideration of the effect of the contact patch size, is no longer as effective as it may have been perceived. Now, this directly affects the actual absorption dynamics and blood levels of the medication in the given patient. Hence in the future, this will be a major factor in a drug's application to therapy. In addition, with the use of any microchip and/or camera to the solid dosage form, the importance of the dosage form not being stuck will increasingly be more important.

We demonstrate the value of minimizing the contact patch surface area in our in vitro trial methods that are discussed in the examples hereto. Our in vitro findings are further supported by in vivo trials disclosed herein.

The initial principle expressed by one embodiment of this invention is that the adhesive contact area of a solid dosage form may be minimized through the use of asymmetric designs—i.e. designs that lack an axis of symmetry. The lack of an axis of symmetry means that the dosage unit cannot be rotated and remain the same form except by rotating 360 degrees to return to the original position. Even an asymmetric shape may of course possess a plane of symmetry as that term is understood in geometry. Low order rotational symmetry, for example, a rotational symmetry of order 4)(90° or order 3 (120°, but preferably an order 2)(180° and most preferably order 1)(360° are also effective at reducing the contact area.

When symmetry is discussed in this case, we mean symmetry about a rotational axis in the center of the dosage form, such axis being perpendicular to a longitudinal axis of the dosage form; it is rotated (not tumbled and not rolled) around this axis for purposes of describing symmetry. Stated another way, if one is looking at the dosage form with its longitudinal axis extending in a horizontal direction, it spins parallel to the horizontal direction as if rotated from either the left or right end.

Now, it should be understood that a standard oblong capsule, caplet shape (one that is typically employed in common products like ibuprofen and the like) possesses order two symmetry. This design is, as we demonstrate, sub-optimal for swallowing. As we demonstrate in other embodiments of the present invention, it is possible to modify symmetric designs—by reducing the contact patch—without destroying symmetry. This can be accomplished providing one has either left a core center annular section in the traditional round mode (which functions as an annulus) and or one rotates one lobe relative to the other lobe. Otherwise the contact patch will not be reduced. As we demonstrate, one can pinch both ends of a conventional oblong tablet and dramatically improve transportability through reduction of the contact patch without destroying the order two symmetry of the dosage form providing that the two ends are out of phase by one degree or greater and/or a central core of the capsule/caplet is left unpinched. By "modification" of the dosage form, we mean the use of indentations (convex, concave and other shaped indentations), twists, bends and other changes that reduce the contact patch area.

We also demonstrate that the use a "bent" dosage form will reduce the contact patch and enhance transit. We show this in the examples with 90° bend. Lesser and greater angles will tend to work as well. However, as the angle approaches 0° then the benefit to reducing the contact patch will also approach zero.

It is demonstrated the reduction of adhesive contact area promotes transit of the dosage form. Furthermore the outward and inward dimpling on asymmetric and symmetric forms is desirable as it lessens contact area. Similarly, an outgoing ridging is also helpful. Inward dimpling is not always desirable as this can form a suctional adhesive force on the mucosa if Laplace pressures are not kept in mind; however, such suction should not be consequential where the dimples are shorter than 3 mm. In such instances the Laplace calculation shows that the pressure should be almost atmospheric.

In another embodiment of the invention, the dosage form can be in the shape of a sphere, preferably, but not necessarily, with dimples, ridges and/or an annular ring. One disadvantage of the sphere is the propensity to roll on a flat surface which can create difficulties, particularly for patients with dexterity issues. In addition a common perception might be that this shape is easier to choke on. The evidence is that this is not so, however, this is a common perception. In addition if one adds dimples and/or ridges and/or an annulus to this form the contact patch will be reduced. Lastly, the aforementioned modifications increase the ability of a water bolus to dislodge and move the dosage unit due to the paddle wheel effect (and the reduced contact patch) which nature uses in something like but not limited to the maple "helicoptor" seed which in nature must be moved readily by water and wind to reach fertile soil. This can be seen if one, in quiet observation, watches these products of nature work themselves off of a solid object like a rock etc.

It may also be desirable to use a surface coating with a relative lubricity factor and a low adhesive characteristic. It may also desirable to use a hydrophobic coating to retard disintegration and subsequent adhesion in the esophagus. A wax like coating, as a non-limitative example could function well as an additional factor. A lubricity agent may be applied by spray coating, film coating and other methods understood could also be an additional factor. It may be desirable to specifically locate the lubricity agent in the annular ring, dimples, ridges or other protrusion. It may also be desirable to use dosage form excipients that are not quick to disintegrate or tack, particularly where the dosage form is not coated as this could be additive to the invention. The key here is to reduce disintegration or surface characteristics that would result in adherence. However, to summarize this topic, first the drug itself must be delivered and therefore the dosage unit must disintegrate and not be so hydrophobic as to adversely interfere with the intended disintegration (typically in the GI tract). In addition, it is important that the material used on the dosage unit surface, as a material from a material science point of view, be as adhesion resistant as possible. After that is accomplished the design as discussed in this application is pivotal.

It may be desirable to use an annular ring wherein the material comprising the annular ring as different disintegration properties than the rest of the composition, i.e. either faster or slower.

Interestingly, while Hey states (and Cooker conjectures) that increased density will enhance tablet transit, we found that reduced density improves transit performance of a solid dosage form through an improved relative buoyancy. This makes logical sense, as the water swallowed has a more beneficial effect if the buoyancy of the dosage form is greater. Density can be controlled through the use of more or less dense excipients (e.g. silicates to lighten as a non-limitative example). The literature demonstrates that a substantial number of esophageal transit issues arise in the case of supine and semi-supine administration. We teach—and demonstrate—that adhesionary forces tend to create transit failure. The low contact patch with additional buoyancy, will—in the presence of water—be kept from substantial contact with the esophageal lining where adhesion can occur (implying a specific gravity of less than one, preferably less than 0.65). This leads to rapid, reliable, successful esophageal transit. It is known that a high number of new drugs NCE's are low dosage potent forms. Thus the possibility exists to give broad access to density modification.

The current invention can be readily made using existing capsule systems, by merely altering the shape of one of the capsule shells. The tableting process can be modified to accommodate the current invention. This would involve a tableting dies that are asymmetric themselves in order to turn out the tablet, capsule, caplet. liquigel etc. Similarly, a ridged die tooling that is female product is counter ridged to resulted in pushed out ridges (or the converse). Dies may also be inward and outward dimpled in order to turn out male/female dimpled forms.

Still another method of manufacturing the current invention is to make a softgel product and then mold the product after conventional manufacture to the desired shape. It may be desirable to adjust the elasticity of the softgel material, as well as reduce the fill level of the softgel as well as modify other parameters in order to minimize the danger of puncture to the softgel during this secondary re-shaping process. Various plasticizers and related agents may be useful for these purposes. In addition there is no need to reduce the fill level if this is a product which is made this way and yet the fill level may be modified.

All of these designs involve some very unique mold forms for the presses and tablet and liquigel and capsule machines that make them. It is intended that the scope of this invention include these molds as well.

Similarly, one may use a secondary re-shaping process with conventional capsules assuming sufficient elasticity (and low fill volume) for the capsule. It is further contemplated that the shape of a conventional, symmetrical dosage may be altered through the use of a sort of prosthesis for tablets, made of GRAS or other acceptable materials. Such a method allows for the use of existing tablet dies and capsule manufacture followed by the secondary addition of the form prosthesis.

Any embodiment of the dosage unit of the present invention may contain an RFID tag antenna or its equivalent. An asymmetric dosage unit also contains an ideal location for an RFID tag antenna or its equivalent and can minimize the tablet substance that the radio wave must traverse. Furthermore, the use of a computer chip can be idealized by using these asymmetric principles shown here. Also, the emerging use of miniature recording cameras for inside the GI tract can benefit from these asymmetric shapes by allowing for better placement of electronics.

An additional aspect of the current invention is that the improved esophageal transit performance of the various designs taught herein allow one to increase the relative load that can be reliably transited. Stated more simply, people have trouble swallowing large tablets and the easing of the swallowing of larger tablets has clear benefits. This also allows for the using of various methods that are otherwise impracticable in a single dosage form, such as low loading sustain release methods like ion exchange or certain coating methods or other binder systems. This further allows for the use of increased amounts of agents to enhance or retard absorption such as buffering agents (including without limitation staged buffering agents), penetration enhancers and other excipients to enhance (and retard) release, delivery and absorption. Also, microchips, smart capsules with a drug reservoir for site specific delivery and/or cameras and other recording devices are more easily swallowed (and size of payload—and thus room for these items can be increased). See Fuisz U.S. Pat. No. 7,899,705 and www.proteusbiomed.com.

The bioactive agent of the present invention is preferably a pharmaceutical but may be any biological, antigen, botanical, food or nutraceutical, cosmaceutical, gene therapeutic or other active agent. It may also comprise a tablet camera or other diagnostic device or drug delivery device that is contemplated to be swallowed.

Examples of pharmaceutical bioactive agents include, but are not limited to ace inhibitors, such as Benazepril, Captopril, Enalapril, Lisinopril, Moexipril, Perindopril, Quinapril, Ramipril and Trandolapril; acne treatments, such as adapalene, azelaic acid, BenzaClin, Benzamycin, Benzoyl Peroxide, clindamycin, Duac, Erythromycin, Glycolic Acid, Isotretinoin, Sulfacetamide with sulfur, Tazarotene and Tretinoin; actinic keratosis, such as declofenac, fluorouracil; addiction aids, such as buprenorphine, Disulfuram, Naltrexone, Suboxone and varenicline; aldosterone antagonists, such as eplerenone and spironolactone; alpha-1 adrenergic blockers, such as alfuzosin, doxazosin, prazosin, tamsulosin and terazosin; ALS agents, such as riluzole; Alzheimer's Disease medications, such as donepezil, Galantamine, rivastigmine, tacrine and memantine; anesthetics, such as dexmedetomidine, etomidate, ketamine, methohexital, pentobarbital, propofol and thiopental; angiotensin II receptor blockers, such as candesartan, eprosartan mesylate, irbesartan, losartan, olmesartan, telmisartan and valsartan; antacids, such as Aluminum hydroxide, AlOH and magnesium trisilicate; anti-arrhythmics, such as adenosine, amiodarone, Atropine, Bretylium, digoxin-Immune Fab, diisopyramide, dofetilide, epinephrine, Esmolol, flecainide, ibutilide, isoproterenol, lidocaine, mexiletine, moricizine, procainamide, propafenone, quinidine, sotalol, tocainide and verapamil; antibiotics, such as Aztreonam, TMP/SMX, Chloramphenicol, Clindamycin, Dapsone, Daptomycin, Ertapenem, Imipenem/cilastatin, Linezolid, Meropenem, Metronidazole, Nitrofurantoin, Quinupristin/Dalfopristin, Rifaximin, Tigecycline, Telithromycin and Tinidazole; anticholinergic acids, such as Dicyclomine, Donnatal, Flavoxate, Glycopyrrolate, Hyoscyamine, Oxybutynin, Propantheline and Tolterodine; anticonvulsants, such as carbamazepine, clonazepam, diazepam, ethosuximide, felbamate, fosphenytoin, gabapentin, levetiracetam, lamotrigine, lorazepam, Oxcarbazepine, Phenobarbital, phenyloin, pregabalin, primidone, tiagabine, topiramate and valproic acid; antidepressants, such as amitriptyline, buproprion, citalopram, desipramine, doxepin, duloxetine, escitalopram, fluoxetine, fluvoxamine, imipramine, mirtazapine, nefazodone, nortriptyline, nortriptyline, sertraline, trazodone and venlafaxine; anti-diarrheals, such as dephenoxylate-Fatropine, Imodium and bismuth subsalicylate; anti-emetics, such as Aprepitant, dolasetron, droperidol, granisetron, metoclopramide, ondansetron, prochlorperazine, scopolamine and trimethobenzamide; antifungals, such as Ampho B, Ampho B lipid, anidulafungin, caspofungin, Clotrimazole fluconazole, flucytosine, Griseofulvin, Itraconazole, ketoconazole, Micafungin, nystatin, Posaconazole, terbinafine, voriconazole, butenafine, ciclopirox, clotrimazole, enconazole, ketoconazole, Miconazole, naftifine, nystatin, oxiconazole terbinafine and Tolnaftate; anti-hepatitis, such as adefovir, entecavir, lamivudine, peginterferon alfa-2a, peginterferon aifa-2b, Rebetron and ribavirin; anti-herpetic agents, such as Acyclovir, famciclovir, valacyclovir, acyclovir, docosanol and penciclovir; antihistamines, such as cetirizine, desloratadine, fexofenadine, loratadine, chiorpheniramine, ciemastine, cyproheptadine, dimenhydrinate, diphenhydramine, hydroxzine and promethazine; anti-hypertension, such as Benazepril & HCTZ, Captopril & HCTZ, Enalapril & HCTZ, Lisinopril & HCTZ, Moexipril & HCTZ, Losartan & HCTZ, Vaisartan & HCTZ, Atenolol & chiorthalidone, Bisoprolol & HCTZ, Metoprolol & HCTZ, Nadolo! & bendrofiumethazide, Propranolol & HCTZ, Timolol & HCTZ, Amlodipine & benazepril, Verapamil & trandolapril, Amiloride & HCTZ, Spironolactone & HCTZ, Triamterene & HCTZ, Clonidine & chiorthalidone, Hydralazine & HCTZ, Methyldopa & HCTZ and Prazosin & polythiazide; anti-hypertensives, such as Aliskiren, Aliskiren, epoprostenol, fenoldopam, hydralazine, minoxidil, nitroprusside, phentolamine and treprostinil; anti-influenza agents, such as amantadine, oseltamivir phosphate, rimantadine and zanamivir; anti-malarials/anti-protozoals/amebicides, such as Atovaquone, Chloroquine, Iodoquinol, Mefloquine, Primaquine, Pyrimethamine, Pyrimethamine-Sulfadoxine and Quinine Sulfate; anti-platelet agents, such as abciximab, dipyridamole/ASA, anagrelide, cilostazol, clopidogrel, dipyridamole, eptifabatide, ticlopidine and tirofiban; antipsychotics, such as aripiprazole, chlorpromazine, Clozapine, fluphenazine, haloperidol, loxapine, molindone, olanzepine, perphenazine, pimozide, quetiapine, risperidone, thioridazine, thiothixine, trifluoperazine, ziprasidone and Lithium; antispasmotics, such as Dicyclomine, Donnatal Extentabs, Propantheline, Simethicone, hyoscyamine, Librax, tegaserod and Bellergal-S; anti-tussives/expectorants, such as Benzonatate and guaifenesin; atopic dermatitis medications, such as pimecrolimus and tacrolimus; benzodiazepines and non-benzodiazepine sedatives, such as aiprazolam, buspirone, chlordiazepoxide, chlorazepate, cionazepam, diazepam, estazolam, eszcpiclone, flurazepam, lorazepam, midazolam, Oxazepam, ramelteon, temazepam, triazolam, zaleplon and zolpidem; beta blockers, such as atenolol, betaxolol, bisoprolol, carvedilol, esmolol, labetalol, metoprolol, nadolol, pindolol, propranolol, sotalol and timolol; bile acid sequestrants, such as cholestyramine, colesevelam and colestipol; bisphosphonates, such as alendronate, etidronate, pamidronate, risedronate, tiludronate and Zoledronic acid, Raloxifene and Teriparatide; bladder spasm medications, such as flavoxate, hyoscyamine, darifenacin, oxybutynin, soiifenacin, tolterodine and trospium; benign prostatic hypertrophy medications, such as alfuzosin, doxazosin, dutasteride, finasteride, tamsulosin and terazosin;

burn preparations, such as mafenide acetate and silver sulfadiazine; calcium channel blockers, such as amlodipine, bepridil, diltiazem, felodipine, isradipine, nicardipine, nifedipine and nisoldipine; calcium supplements, such as Calcium and Hypocalcemia; cephalosporins, such as Cefadroxil, Cefazolin, Cephradine, Cephalexin, Cefaclor, Cefotetan, Cefoxitin, Cefprozil, Cefuroxime, Cefuroxime, loracarbef, Cefdinir, Cefixime, Cefoperazone, Cefotaxime, Cefpodoxime, Ceftazidime, Ceftibuten, Ceftizoxime and Cefepime; colony stimulating factors, such as darbepoietin alfa, erythropoietin, filgrastim, oprelvekin, pegfilgrastim and sargramostim; corticosteroids, such as Budesonide, cortisone acetate, dexamethasone, fludrocortisones, hydrocortisone, methylprednisolone and prednisone; corticosteroids Intra-articular, such as Depo-Medrol and Triamcinolone Acetonide; cystitis, such as pentosan polysulfate, Bethanecol and Alum irrigation; decongestants, such as Phenylephrine and Pseudoephedrine; anti-diabetic agents, such as acarbose, Miglitol and metformin, Avandamet®, Glucovance, Metaglip, Metaglip, rosiglitazone, osiglitazone, repaglinide, Chlorpropamide, glimepiride, glyburide, glipizide, Tolazamide, Tolbutamide, Glucagon, extenatide and pramlintide; direct thrombin inhibitors, such as argatroban, Bivalirudin and lepirudin; disease modifying agents, such as adalimumab, anakinra, auranofin, azathioprine, etanercept, hydroxychloroquine, infliximab, leflunomide, methotrexate and sulfasalazine; diuretics, such as Acetazolamide, Amiloride, Amiloride and HCTZ Bendroflumethiazide, Bumetanide, Chlorothiazide, Chlorthalidone, Dichlorphenamide, Eplenerone, Ethacrynic acid, Furosemide, Hydrochlorothiazide, HCTZ rrriampterene, Hydroflumethiazide, Indapamide, Methazolamide, Methyclothiazide, Methyclothiazide, Metolazone, Polythiazide, Spironolactone, Spironolactone, HCTZ Torsemide, Trichlormethiazide and Triamterene; endocrine agents, such as bromoc cinacalcet cosyntropin, riptine, cabergoline, calcitonin, desmopressin, Leuprolide, octreotide and vasopressin; erectile dysfunction agents, such as Sildenafil, tadalafil, vardenafil; fever medications, such as allopurinol, antihistamines, azathioprine, barbiturates, carbamazepine, cephalosporins, cimetidine, folic acid, hydralazine, hydroxyurea, ibuprofen, isoniazid, methyldopa, nitrofurantoin, penicillins, phenyloin, phenyloin, procainamide, propylthiouracil, quinidine, streptomycin sulfonamides, sulindac, triamterene and vancomycin; fibrates, such as clofibrate, fenofibrate and gemfibrozil; fluoroquinolones, such as Ciprofloxacin, Gatifloxacin, Levofloxacin, Moxifloxacin, Norfloxacin and Ofloxacin; gastrointestinal agents, such as Alosetron, infliximab, Mesalamine, misoprostol, Neomycin, octreotide, osaiazine, Orlistat, sucralafate, Sulfasalazine and vasopressin; gout treatments, such as allopurinol, coichicine, probenecid, Rasburicase and sulfinpyrazone; H2 receptor blockers, such as cimetidine, famotidine, nizatidine and ranitidine; Anti-herpetic agents, such as Acyclovir, famciclovir, valacyclovir, acyclovir, docosanol and penciclovir; hypertensive urgency, such as Captopril, Clonidine and Labetalol; hypertensive emergency, such as Enalaprilat, Esmolol, Fenoldopam mesylate, Hydralazine, Labetalol, Nicardipine, Nitroglycerin and Sodium nitroprusside; hemorrhoidal preparations, such as Anusol HC, Anusol Suppository, Dibucaine, pramoxine 1%, Proctofoam-HC and Analpram-HC; inflammatory bowel disease agents, such as balsalazide, budesonide, infliximab, mesalamine, olsalazine and sulfasalazine; Interferon, such as Interferon Alfa-2A, Interferon Alfa-2b, Interferon Alfa-2b and Ribavirin combo Pack, Interferon Alfa-N3, Interferon Beta-1A, Interferon Beta-1B (Betaseron); intermittent claudication, such as ciiostazol and pentoxifylline; immunizations, such as Comvax, diphtheria-tetanus toxoid, Hepatitis A vaccine, Hepatitis B vaccine, Influenza vaccine, Fluzone, Lyme disease vaccine, PNEUMOVAX* 23; laxatives, such as Bisacodyl, Cascara, Docusate, Fleet Phospho-Soda, Glycerin, Lacalutose, lubiprostone, Magnesium citrate, Magnesium hydroxide—MOM, Mineral Oil, Pericolace, Psyllium and Senna; low molecular weight heparins, such as dalteparin, danaparoid, enoxaparin, tinzaparin, fondaparinux; macrolides, such as Azithromycin, Clarithromycin and Erythromycin; magnesium, such as magnesium salt; migraine treatments, such as almotriptan, eletriptan, frovatriptan, naratriptan, rizatriptan, sumatriptan, zolmitriptan, Cafergot®, Cafergot®, dihydroergotamine and Midrin®; mouth and lip treatments, such as amlexanox, Benzocaine, carbamide, peroxide, Kenalog in Orabase®, Phenol, chlorhexidine gluconate, clotrimazole, Nystatin, Penciclovir, docosanol, Gelclair, lidocaine viscous, BMX Cocktail, Pilocarpine and Artificial saliva; multiple sclerosis treatments, such as glatiramer, interferon beta-1A and interferon beta-1 B; muscle relaxants, such as baclofen, carisprodol, cyclobenzaprine, cyclobenzaprine, Diazepam, Metaxalone, Methocarbamol, Orphenadrine; nasal preparations, such as azelastine, beclomethasone, budesonide, cromolyn, desmopressin acetate, flunisolide, fluticasone, Ipratropium bromide, mometasone, oxymetazoline, phenylephrine, Saline nasal spray, Sumatriptan, triamcinolone and Zolmitriptan; urology treatments, such as Belladonna and opium, flavoxate, hyoscyamine, hyoscyamine, oxybutynin, solifenacin, tolterodine and trospium; neuromuscular blockers, such as Atracurium, Cisatracurium, doxacurium, mivacurium, pancuronium, Rocuronium, Succinylcholine, vecuronium, Mivacurium, Rapacuronium, Rocuronium, Succinylcholine, Atracurium, Cisatracurium, Pancuronium, Vecuronium, Doxacurium, Pipecuronium and Tubocurarine; nitrates, such as Isosorbide dinitrate, Isosorbide mononitrate, Nitroglycerin ointment, Nitrobid and Nitroglycerin transdermal; NSAID's, such as Arthrotec, diclofenac, Etodolac, indomethacin, Ketorolac, Sulindac, Tolmentin Diflunisal Salsalate Meloxicam, piroxicam, Nabumetone Flurbiprofen, Ibupropen, Ketoprofen, Naproxen, Oxaprozin, celecoxib, Rofecoxib and Valdecoxib; ophthalmic agents, such as, proparacaine, tetracaine, Ciprofloxacin, Erythromycin, Gentamcyin, levofloxacin, levofloxacin, norfloxacin, Ofloxacin, Polysporin®, Polytrim, Sulfacetamide, Tobramycin, Blephamide®, Blephamide®, Maxitrol®, Pred G® and TobraDex®, Dexamethasone, Fluorometholone, Loteprednol, Prednisone, Rimexolone, azelastine, Cromolyn sodium, emedastine, Epinastine, Ketotifen Fumarate Ophthalmic Solution 0.025.degree./o, Levocabastine, Lodoxamide tromethamine, Naphazoline, Naphcon-A®, nedocromil, Olopatadine, pemirolast, Betaxolol, Betaxolol, Levobunolol, TimoloE, Brinzolamide, Dorzolamide, Pilocarpine, bimatoprost, Latanoprost, travoprost, unoprostone, Apraclonidine, Brimonidine, Cosopt® and Cosopt®, Atropine, Cyclopentolate, Homatropine, Phenylephrine, Phenylephrine, Diclofenac, Flurbiprofen and Ketorolac; ear (otic) preparations, such as Auralgan®, carbamide peroxide, CIPRODEX®, Ciprofloxacin and hydrocortisone, Cortisporin®, Ofloxacin, Triethanolamine and Vosol Otic®; opiates, such as Codeine Fentanyl Hydrocodone Hydrocodone, Meperidine Methadone, morhphine, xycodone, Propoxyphene, Darvon®, Fioricet, Fiorinal, Soma compound, Tramadol, Anexsia, Darvocet, Darvon Compound, Lorcet, Lortab, Percocet, Percodan, Roxicet, Tylenol with Codeine, Tylox, Vicodin, Wygesic, Buprenorphene, Butorphanol, Dezocine, Nalbuphine, Pentazocine, Nalmefene Naloxone, Suboxone® and Ziconotide; parkinson's disease treatments, such as amantadine, benztropine, bromocriptine, entacapone, pergolide, pramipexole, ropinirole, selegiline, Sinemet®, tolcapone and trihexyphenidyl; PCA—Patient Controlled Analgesia, such as Fentanyl, Hydromorphone, Meperidine and Morphine; penicillin's, such as Ampicillin, Ampicillin/sulbactam, Amoxicillin, Amoxicillin/Clavulanate, Cloxacillin, Dicloxacillin, Nafcillin, Penicillin G, Penicillin VK, Piperacillin, Piperacillin/Tazobactamm, Ticarcillin, and Ticarcillin/Clavulanate; phosphate supplementation, such as, K-Phos® Neutral Tablets, K-PHOS® ORIGINAL, NeutraPhos®; potassium supplementation, such as K-LOR, KlorCon®, Potassium depletion; prostate cancer medications, such as bicalutamide, flutamide, gosereiin, leuprolide and nilutamide; proton pump inhibitor's, such as esomeprazole, Lansoprazole, Omeprazole, Pantoprazole and Rabeprazole Sodium; psoriasis medications, such as acitretin, aiefacept, Anthralin, Caicipotriene, efalizumab and Tazarotene; renal failure medications, such as Aluminum Hydroxide, Calcium acetate, Calcitriol, Doxercalciferol, Ferric Sodium Gluconate, paricalcitol and sevelamer; pulmonary medications, such as ipratropium, tiotropium, albuterol, bitolterol, levalbuterol, pirbuterol, metaproterenol, formoterol, salmeterol, Advair®, Symbicort®, beclomethasone, budesonide, flunisofide, fluticasone, Mometasone furoate, triamcinolone, montelukast Singulair®, zafirlukast, cromolyn sodium, nedocromil, acetylcysteine and aminophylline/theophylline; disease modifying agents, such as adalimumab, anakinra, auranofin, azathioprine, etanercept, hydroxychloroquine, infliximab, leflunomide, methotrexate and sulfasalazine; HMG COA reductase inhibitors, such as Atorvastatin, Fluvastatin, Lovastatin, Pravastatin, Rosuvastatin, Simvastatin, Advicor®, Vytorin® and ezetimibe; stimulants, such as atomoxetine, benzphetamine, Caffeine, dexmethylphenidate, Dextroamphetamine, diethylpropion, Methylphenidate, Modafinil, Pemoline, phendimetrizine, phentermine and sibutramine; tetracyclines such as Doxycycline, Minocycline and Tetracycline; thrombolytic agents such as Alteplase; anti-thyroid agents such as methimazole and propylthiouracil; toxicology related medications such as acetylcysteine, Charcoal, deferoxamine, digoxin immune fab, flumazenil, fomepizole, methylene blue, naloxone, sodium polystyrene sulfonate and Sorbitol; anti-mycobacterial agents such as Ethambutol, Isoniazid, Pyrazinamide, rifabutin, Rifamate, Rifampin, Rifapentine and Rifater; topical products such as Alitretinoin, Becaplermin, Calamine, Capsaicin, Doxepin, lidocaine/prilocaine, fluorouracil, Masoprocol, Pimecrolimus, Selenium sulfide and Tacrolimus; topical anti-viral agents such as acyclovir, docosanol, imiquimod, penciclovir, podofilox and podophyllin; topical antibacterials such as bacitracin, metronidazole, mupirocin, bacitracin/neomycin/polymyxin, bacitracin/polymyxin and silver sulfadiazine; topical antifungals such as butenafine, ciclopirox, clotrimazole, econazole, ketoconazole, miconazole, naftifine, nystatin, oxiconazole, terbinafine and tolnaftate; topical anti-parasitic agents such as Crotamiton, Lindane, Permethrin, pyrethrins and piperonyl butoxide; topical burn preparations such as mafenide acetate and silver sulfadiazine; topical corticosteroids such as Aclometasone dipropionate, Desonide, Flucinolone acetonide, Hydrocortisone, Betamethasone dipropionate, betamethasone valerate, clocortolone pivalate, desoximetasone, fluocinolone acetonide, flurandrenolide, fluticasone propionate, Chydrocortisone butyrate, hydrocortisone valerate, mometasone furoate, prednicarbate, triamcinoione, amcinonide, augmented betamethasone dipropionate, betamethasone dipropionate, desoximetasone, diflorasone diacetate, fluocinalone acetonide, fluocinonide, halcinonide, clobetasol propionate, difiorasone diacetate and haiobetasol propionate; urology medications such as pentosan polysulfate, Bethanecol and phenazopyridine; vaginal preparations such as clindamycin, metronidazole, butoconazoie, clotrimazole, miconazoie, terconazole and tioconazole; vasodilators such as Fenoldopam mesylate, Hydralazine, Nesiritide, Nicardipine, Nitroglycerin, and Sodium Nitroprusside; and vasopressors and inotropes such as Dobutamine, Dopamine, Epinephrine, inamrinone, Milrinone, Norepinephrine, Phenylephrine, and Vasopressin.

Examples of food or nutraceutical bioactive agents include, but are not limited to, constituents in foods or dietary supplements that are responsible for changes in health status, such as components of plants, especially fruits and vegetables, e.g., soy which contains isoflavones and phytoestrogens, tomatoes which contain lycopene that may have anticancer properties, berries such as blueberries and raspberries which contain flavonoids like anthocyanins that may act as antioxidants, green tea which contains epigallocatechin gallate (EGCG) that may have anticancer properties, resveratrol from red grape products as an antioxidant, soluble dietary fiber products, such as psyllium seed husk for reducing hypercholesterolemia, broccoli (sulforaphane) as a cancer preventative, and soy or clover (isoflavonoids) to improve arterial health. Flavonoids, antioxidants, alpha-linolenic acid from flax seeds, extracts such as ginseng, garlic oil, etc. Examples of biological bioactive agents include, but are not limited to biologically active substances in plants that have proven (e.g. cholesterol lowering effects of phytosterols) or potential beneficial effects on health, i.e., phytochemicals or phytonutrients, in particular phytochemicals in leaves, stems, roots, tubers, buds, fruits, seeds and flowers, and plant derived foods and drinks (such as tea, coffee, alcoholic beverages), such as flavonoids found in a range of plant derived foods including tea, wine, onions, apples and berries, glucosinolates from Cruciferous vegetables, phenolic acids in tea and coffee for example, and carotenoids (some of which are precursors of vitamin A) prevalent in red, green and orange fruits and vegetables.

Examples of antigen bioactive agents include, but are not limited to exogenous antigens, endogenous antigens, autoantigens and tumor antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells (CD4.sup.+) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection. The fragments are then presented on the cell surface in the complex with MHC class I molecules. If activated cytotoxic CD8+ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. An autoantigen is usually a normal protein or complex of proteins (and sometimes DNA or RNA) that is recognized by the immune system of patients suffering from a specific autoimmune disease. These antigens should, under normal conditions, not be the target of the immune system, but, due to mainly genetic and environmental factors, the normal immunological tolerance for such an antigen has been lost in these patients. Tumor antigens or Neoantigens are those antigens that are presented by MHC I or MHC II molecules on the surface of tumor cells. These antigens can sometimes be presented by tumor cells and never by the normal ones. In this case, they are called tumor-specific antigens (TSAs) and, in general, result from a tumor-specific mutation. More common are antigens that are presented by tumor cells and normal cells, and they are called tumor-associated antigens (TAAs). Cytotoxic T lymphocytes that recognize these antigens may be able to destroy the tumor cells before they proliferate or metastasize. Tumor antigens can also be on the surface of the tumor in the form of, for example, a mutated receptor, in which case they will be recognized by B cells.

Examples of botanical bioactive agents include, but are not limited to PMI-004 (advanced botanical formulation for type II diabetes—Represents a multi-mechanism bioactive that: 1) in adipocytes increases adiponectin secretion, 2) in the liver lowers PEPCK expression, and 3) in muscle cells increases cellular signaling through the insulin receptor pathway, increasing glucose uptake, glycogen synthase, and glycogen accumulation), PMI-005 (botanical bioactive, derived from a common vegetable, that inhibits gene expression of a variety of pro-inflammatory cytokines (including a-TNF, i-NOS, 1 L-1b, and COX-2). Currently undergoing a human clinical trial in osteoarthritis. Also may have utility in the management of severe/life threatening inflammatory conditions, such as in the management of the septic patient), PMI-006 (botanical bioactive, derived from a spice, that inhibits a range of inflammation-related enzymes (including a-TNF and COX-2). Also possesses range of novel bioactivities related to both lipid and glucose metabolism (RXR receptors)), PMI-007 (a powerful, centrally acting, botanical appetite suppressor which acts via a unique central pathway in the nutrient-sensing hypothalamic neurons by increasing ATP content/production. It possesses potent anorectic activity without typical CNS appetite suppressor side effects. Pre-clinical data has shown that the agent suppresses both appetite and reduces weight in animal models, while there is supporting clinical evidence of human efficacy), PMI-008 (botanical bioactive, derived from an agricultural waste processing stream, that blocks fat accumulation/absorption and promotes weight loss via interaction with a variety of lipases including PL, LPL, and HSL), and PMI-016 (a powerful, plant-derived anabolic/ergogenic agent, with no androgenic side effects; could be used in a range of human muscle wasting disorders, including those associated with both cancer and AIDS, as well as general aging (sarcopenia). This agent has been shown to induce protein synthesis in muscle cells (similar to IGF) and promote a reduction in protein degradation, while it has also been shown to increase growth hormone gene transcription and decrease in ubiquitin protein ligase gene transcription. PM1-016 shows no binding to testosterone receptor in contrast to anabolic steroids).

The FDA defines drugs as products that "cure, treat, mitigate or prevent disease or that affect the structure or function of the human body." Cosmetic products are defined by the FDA as "articles intended to be rubbed, poured, sprinkled, or sprayed on, introduced into, or otherwise applied to the human body . . . for cleansing, beautifying, promoting attractiveness, or altering the appearance." Although cosmaceutical products have properties of both groups, the FDA lumps them under the definition of cosmetics, and they are not recognized as a distinct category. Because cosmaceutical products are not included in the FDA's definition of drugs, they are not subject to the same regulations, restrictions, and testing.

It should be noted that on those dosage units that are medically appropriate to break into, e.g., two (or more) equal dosage forms, a traditional score mark can be present. Based on the above, that score mark may or may not be in the traditional location, i.e., in the middle of the dosage unit, but can be at a location that divides the dosage unit into two (or more) equal volumes. While spherical or ball-like dosage units (with and/or without dimples and ridges) can theoretically be scored, the spherical shape makes it difficult to cleave. Adding an annular ring makes it even more difficult to cleave a sphere. Thus, a spherical dosage unit (with and/or without dimples, ridges and/or an annular ring) is most appropriate for dosage units that are medically not intended to be broken or cleaved.

FIG. 1A is a perspective view of one embodiment of an oral dosage unit of the present invention; FIG. 1B is a top plan view thereof; and FIG. 1C is a front elevation view thereof (looking from an angle 90° from that of FIG. 1B). FIGS. 1A-1C show a "modified" gel cap or tablet 10 that has been modified by to render the gel cap pinched (thinner) at one end 12 (the left end shown in these figures). The other end 14 (the right end in the figures) can, in this embodiment, retain its standard, e.g., generally cylindrical form, as can be seen from FIGS. 1B and 1C. In the embodiment shown in FIGS. 1A-1C, as an example only, the pinched (thinner) 12 is wider than the other end 14 (see, FIG. 1B). The modified gel cap or tablet 10 is asymmetric. Thus, FIGS. 1A-1C show an asymmetric oral dosage unit 10 that is asymmetric with respect to a rotational axis RA in the center (center meaning the mid portion along the longitudinal axis) of the dosage unit, the rotational axis RA being perpendicular to a longitudinal axis of the dosage form. If desired, both ends of the dosage unit 10 can be made pinched or thinner if the pinched or thinned ends are more than 0° and less than 180° out of phase with respect to the longitudinal axis.

In the asymmetric oral dosage unit of FIGS. 1A-1C, the dosage unit 10 has opposing end portions 12 and 14 along the longitudinal axis, one end portion 14 having a substantially cylindrical shape and an opposite end portion 12 having a flattened area with a thickness smaller than an a radius of the cylindrical portion 14.

FIG. 2A is a top plan view of another embodiment of an oral dosage unit of the present invention; FIG. 2B is a front elevation view thereof (looking from an angle 90° from that of FIG. 2A); and FIG. 2C is a cross-sectional view along lines 2C-2C of FIG. 2A.

FIGS. 2A-2C show a "modified" gel cap, capsule or tablet 20 that has been modified by to render the gel cap, capsule or tablet pinched (thinner) at one end 22 (the left end shown in these figures) and to have a concave depression 23. The other end 24 (the right end in the figures) can, in this embodiment, retain its standard, e.g., generally cylindrical form, as can be seen from FIGS. 2B and 2C. In the embodiment shown in FIGS. 2A-2C, as an example only, the pinched (thinner) 22 is wider than the other end 24 (see, FIG. 2A). The modified gel cap or tablet 20 is asymmetric. Thus, FIGS. 2A-2C show an asymmetric oral dosage unit 20 that is asymmetric with respect to a rotational axis RA in the center of the dosage unit, the rotational axis RA being perpendicular to a longitudinal axis of the dosage form. If desired, both ends of the dosage unit 20 can be made pinched or thinner and one or both ends can have concave depressions, if the pinched or thinned ends are more than 0° and less than 180° out of phase with respect to the longitudinal axis.

While FIGS. 2A-2C show a gel cap, capsule or tablet 20 having a concave depression 23, it can alternatively have a convex protrusion instead of the concave depression 23.

FIG. 3A is a perspective view of still another embodiment of an oral dosage unit of the present invention; FIG. 3B is a top plan view thereof; and FIG. 3C is a front elevation view thereof (looking from an angle 90° from that of FIG. 3B).

FIGS. 3A-3C show a "modified" gel cap, capsule or tablet 30 that has been modified by to render the gel cap, capsule or tablet pinched (thinner) at both ends 32 and 34 and to have concave depressions 33 and 35. The pinched or thinned ends are more than 0° and less than 180° out of phase with respect to the longitudinal axis, i.e., 90° out of phase with respect to the longitudinal axis in this embodiment. In this embodiment, none of the gel cap or tablet has a standard, e.g., generally cylindrical form. The modified gel cap or tablet 30 is asymmetric. Thus, FIGS. 3A-3C show an asymmetric oral dosage unit 30 that is asymmetric with respect to a rotational axis RA in the center of the dosage unit, the rotational axis RA being perpendicular to a longitudinal axis of the dosage form.

While FIGS. 3A-3C show a gel cap, capsule or tablet 30 having concave depressions 33 and 35, it can alternatively have convex protrusions instead of the concave depressions 33.

Figure 4B:
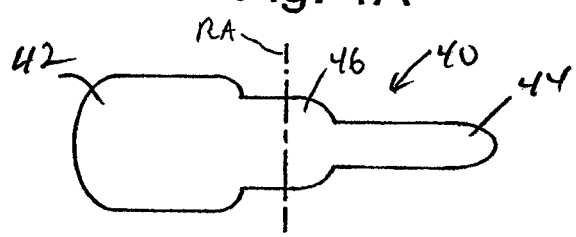
FIG. 4B is a front elevation view thereof (looking from an angle 90° from that of FIG. 4A)

FIG. 4A is a top plan view of yet another embodiment an oral dosage unit of the present invention; FIG. 4B is a front elevation view thereof (looking from an angle 90° from that of FIG. 4A); and FIG. 4C is a right side elevation view (looking from an angle 90° from that of FIG. 4A and 90° from that of FIG. 4B).

Figure 4C:
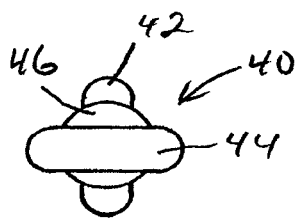
FIG. 4C is a right side elevation view (looking from an angle 90° from that of FIG. 4A and 90° from that of FIG. 4B).

FIGS. 4A-4C show a "modified" gel cap or tablet 40 that has been modified by to render the gel cap pinched (thinner) at both ends 42 and 44. The pinched or thinned ends 42, 44 are more than 0° and less than 180° out of phase with respect to the longitudinal axis, i.e., 90° out of phase with respect to the longitudinal axis in this embodiment. In this embodiment, the middle section 46 (along the longitudinal axis) of the gel cap or tablet has a standard, e.g., generally cylindrical form. The modified gel cap or tablet 40 is asymmetric. Thus, FIGS. 4A-4C show an asymmetric oral dosage unit 40 that is asymmetric with respect to a rotational axis RA in the center of the dosage unit, the rotational axis RA being perpendicular to a longitudinal axis of the dosage form.

Figure 5A:
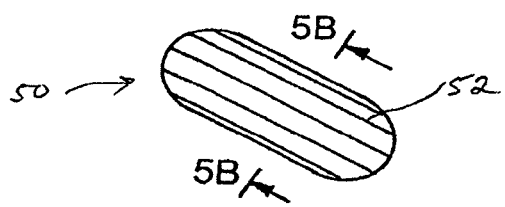
FIG. 5A is a perspective view of still another embodiment an oral dosage unit of the present invention.
Figure 5B:
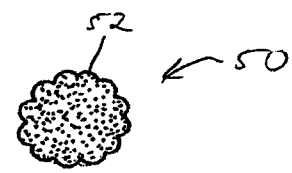
FIG. 5B is a cross-sectional view along lines 5B-5B of FIG. 5A.

FIG. 5A is a perspective view of still another embodiment an oral dosage unit of the present invention; and FIG. 5B is a cross-sectional view along lines 5B-5B of FIG. 5A.

FIGS. 5A and 5B show a "modified" gel cap or tablet 50 that has ridges 52 running longitudinally on the periphery of the dosage unit 50. The ridges 52 and valleys between the ridges 52 reduce the contact patch of the dosage unit 50 with a flat surface compared to non-ridged dosage unit of the same size and shape. While the ridges 52 run longitudinally on the periphery of the dosage unit 50 in this embodiment, the ridges 52 need not run longitudinally but may be provided, e.g., concentrically or spirally as long as the ridges 52 reduce the contact patch of the dosage unit 50 with a flat surface compared to non-ridged dosage unit of the same size and shape.

Figure 6A:
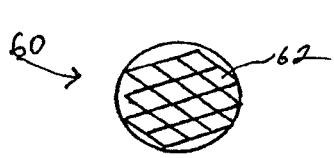
FIG. 6A is a top plan view of yet another embodiment of an oral dosage unit of the present invention.
Figure 6B:
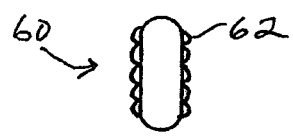
FIG. 6B is a side elevation view thereof (looking from an angle 90° from that of FIG. 4A and 90° from that of FIG. 6A).

FIG. 6A is a top plan view of yet another embodiment of an oral dosage unit of the present invention; and FIG. 6B is a side elevation view thereof (looking from an angle 90° from that of FIG. 4A and 90° from that of FIG. 6A).

The oral dosage unit 60 shown in FIGS. 6A and 6B has opposing outer major surfaces having convex dimples 62 so as to reduce the contact patch of the dosage unit 60 with a flat surface compared to dosage unit of the same size and shape but without dimples. The dimples can also be concave.

Figure 7A:
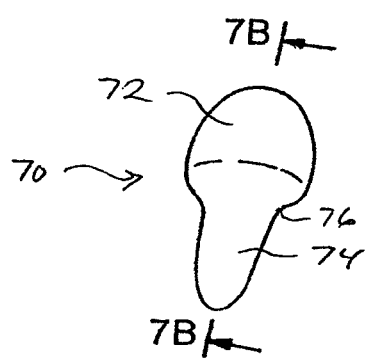
FIG. 7A is a perspective view of still another embodiment an oral dosage unit of the present invention.
Figure 7B:
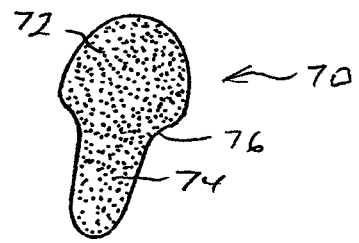
FIG. 7B is a cross-sectional view along lines 7B-7B of FIG. 7A.

FIG. 7A is a perspective view of still another embodiment an oral dosage unit of the present invention; and FIG. 7B is a cross-sectional view along lines 7B-7B of FIG. 7A.

The oral dosage unit 70 of FIGS. 7A and 7B has a bulbous shape in which one end 72 is enlarged with respect to another end 74. While this dosage unit 70 is symmetric about its longitudinal axis, it is asymmetric about a rotational axis perpendicular to its longitudinal axis, so as to reduce the contact patch with respect to a flat surface; i.e., area 76 will not come into contact with a flat surface.

As noted previously, the dosage form can be a in the shape of a sphere. Applicants have found that this shape reduces the contact patch with a flat surface. In one embodiment of the present invention, the sphere does not have dimples, ridges and/or an annular ring. On the other hand, to reduce the propensity to roll on a flat surface and to further reduce the contact patch, other embodiments of the present invention may include dimples, ridges and/or at least one annular ring provided on an outer surface of the spherical dosage unit.

Figure 8A:
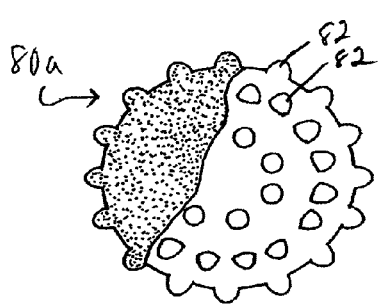
FIG. 8A is a partially broken away plan view of yet another embodiment of the present invention showing a spherical oral dosage unit of the present invention.

FIG. 8A is a partially broken away plan view of yet another embodiment of the present invention showing a spherical oral dosage unit of the present invention. In FIG. 8A, the spherical oral dosage unit 80a has convex dimples 82 provided on its outer surface.

Figure 8B:
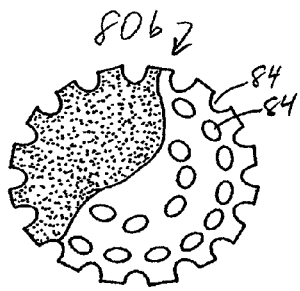
FIG. 8B is a partially broken away plan view of yet another embodiment of the present invention showing a spherical oral dosage unit of the present invention containing a variation of the embodiment of FIG. 8A.

FIG. 8B is a partially broken away plan view of yet another embodiment of the present invention showing a spherical oral dosage unit of the present invention containing a variation of the embodiment of FIG. 8A. In FIG. 8A, the spherical oral dosage unit 80b has convex dimples 84 provided on its outer surface.

Figure 8C:
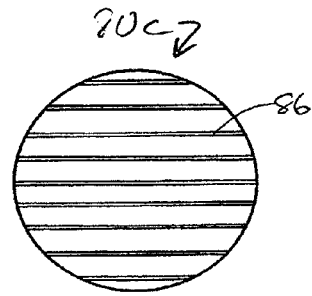
FIG. 8C is a plan view of yet another embodiment of the present invention showing a spherical oral dosage unit of the present invention containing a variation of the embodiments of FIGS. 8A and 8B.

FIG. 8C is a plan view of yet another embodiment of the present invention showing a spherical oral dosage unit of the present invention containing a variation of the embodiments of FIGS. 8A and 8B. In FIG. 8C, the spherical oral dosage unit 80c has ridges 86 provided on its outer surface.

Figure 8D:
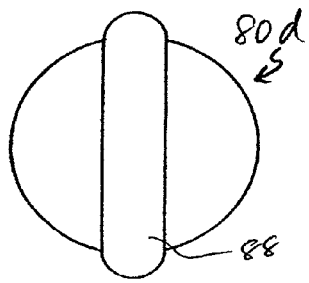
FIG. 8D is a plan view of yet another embodiment of the present invention showing a spherical oral dosage unit of the present invention containing a variation of the embodiments of FIGS. 8A, 8B and 8C.

FIG. 8D is a plan view of yet another embodiment of the present invention showing a spherical oral dosage unit of the present invention containing a variation of the embodiments of FIGS. 8A, 8B and 8C. In FIG. 8D, the spherical oral dosage unit 80d has an annular ring 88 provided around its outer surface.

Figure 8E:
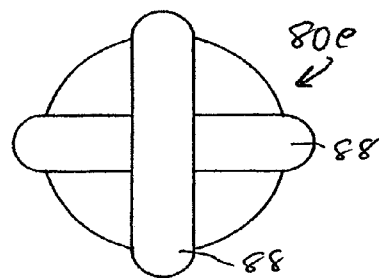
FIG. 8E is a plan view of yet another embodiment of the present invention showing a spherical oral dosage unit of the present invention containing a variation of the embodiments of FIGS. 8A, 8B, 8C and 8D.

FIG. 8E is a plan view of yet another embodiment of the present invention showing a spherical oral dosage unit of the present invention containing a variation of the embodiments of FIGS. 8A, 8B, 8C and 8D. In FIG. 8E, the spherical oral dosage unit 80e has pair of annular rings 88 provided around its outer surface and intersecting at 90° from each other.

Figure 9A:
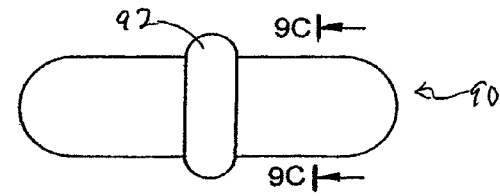
FIG. 9A is a top plan view of still another embodiment of an oral dosage unit of the present invention.
Figure 9B:
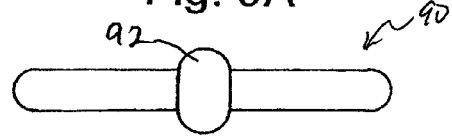
FIG. 9B is a front elevation view thereof (looking from an angle 90° from that of FIG. 9A)
Figure 9C:
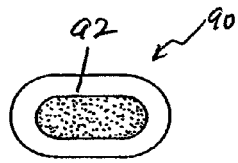
FIG. 9C is a cross-sectional view along lines 9C-9C of FIG. 9A.

FIG. 9A is a top plan view of still another embodiment of an oral dosage unit of the present invention; FIG. 9B is a front elevation view thereof (looking from an angle 90° from that of FIG. 9A); and FIG. 9C is a cross-sectional view along lines 9C-9C of FIG. 9A. In the embodiment of FIGS. 9A-9C, an oral dosage unit in a typical shape of a caplet 90 is modified to have an annular ring 92 provided around its outer surface at a middle portion along its longitudinal axis.

Figure 10A:
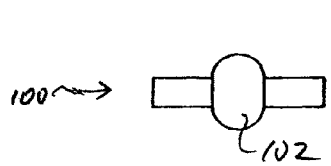
FIG. 10A is a front elevational view of yet another embodiment of an oral dosage unit of the present invention.
Figure 10B:
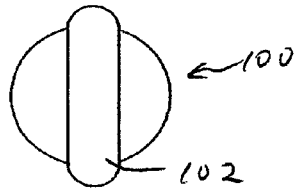
FIG. 10B is a top plan view thereof (looking at an angle 90° from that of FIG. 10A).

FIG. 10A is a front elevational view of yet another embodiment of an oral dosage unit of the present invention; and FIG. 10B is a top plan view thereof (looking at an angle 90° from that of FIG. 10A). In the embodiment of FIGS. 10A and 10B, an oral dosage unit in a typical shape of a disc-shaped tablet (circular in plan view) 100 is modified to have an annular ring 102 provided around its outer surface at a central portion.

While the annular ring is shown in FIGS. 8D, 8E, 9A-9C, 10A and 10B around a middle portion of the dosage unit, the location is not limited to the middle portion.

Viewed in another way, if, on a unidimensional flat surface, the contact measurement of a dosage form contact patch that is touching a flat surface is 1 to 1 with a starting non-modified symmetrical dosage unit. As soon as one takes that dosage unit with the same total volume and 1) makes it asymmetric and/or 2) makes it ridged and/or dimpled and/or 3) uses a raised annular ring, then the ratio of the contact patch becomes less than 1 to 1 compared to the non-modified form of the same volume and shaped (without the modification) dosage unit.

It is also possible to reduce the contact patch of a dosage unit with a flat surface, at least with respect to some orientations of the dosage form, by bending the dosage unit, either retaining its symmetry or making it asymmetric.

Of course, the present invention relates to dosage forms modified from another form and dosage forms originally manufactured in the modified shape.

Figure 11A:
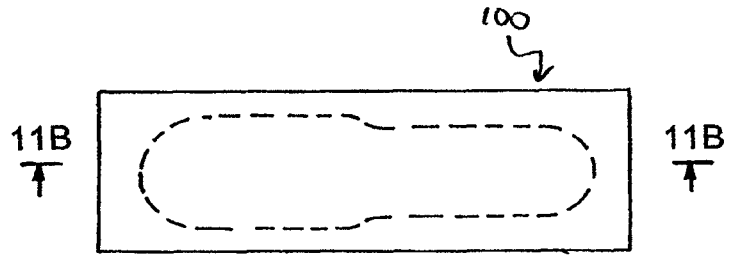
FIG. 11A is a top plan view of one example of a die for forming one example of an oral dosage unit of the present invention.
Figure 11B:
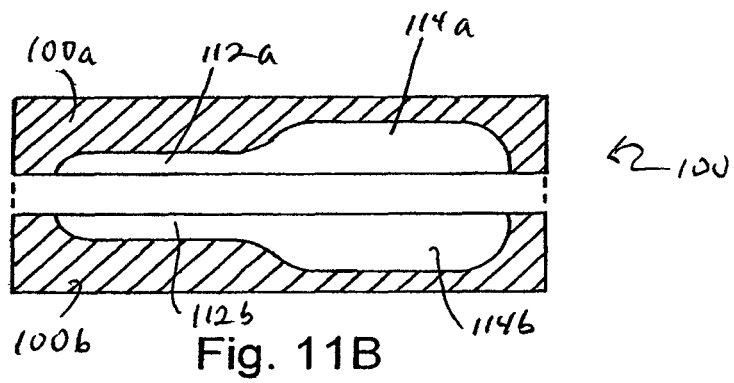
FIG. 11B is a cross-sectional view thereof along line 11B-11B of FIG. 11A.

FIG. 11A is a top plan view of one example of a die for forming one example of an oral dosage unit of the present invention and FIG. 11B is a cross-sectional view thereof along line 11B-11B of FIG. 11A. The die 100 has top and bottom die halves 100a, 100b having respective cavities that, in a closed state of the die, correspond to the shape of a tablet of a shape corresponding to tablet 10 shown in, e.g., FIGS. 1A-1C. The cavity is shown in dashed lines in FIG. 11A. The cavity in the top portion 100a includes cavity portions 112a and 114a; the cavity in the bottom portion 100b includes cavity portions 112b and 114b. As can be seen from FIGS. 11A and 11B, the die 100 can be used as would be understood by those skilled in the art so that cavity portions 112a and 112b form portion 12 of tablet 10 and cavity portions 114a and 114b form portion 14 of tablet 10.

Figure 12A:
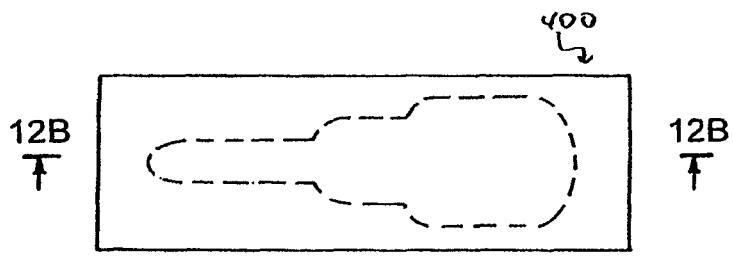
FIG. 12A is a top plan view of one example of a die for forming another example of an oral dosage unit of the present invention.
Figure 12B:
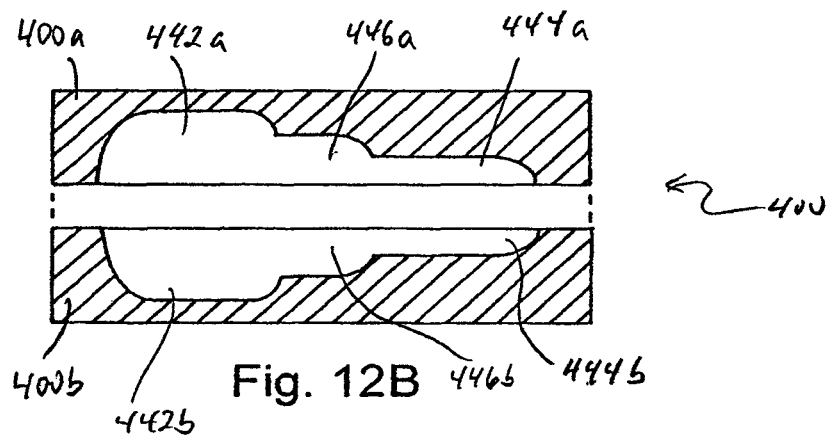
FIG. 12B is a cross-sectional view thereof along line 12B-12B of FIG. 12A.

FIG. 12A is a top plan view of one example of a die for forming another example of an oral dosage unit of the present invention and FIG. 12B is a cross-sectional view thereof along line 12B-12B of FIG. 12A. The die 400 has top and bottom die halves 400a, 400b having respective cavities that, in a closed state of the die, correspond to the shape of a tablet of a shape corresponding to tablet 40 shown in, e.g., FIGS. 4A-4C. The cavity is shown in dashed lines in FIG. 12A. The cavity in the top portion 400a includes cavity portions 442a, 444a and 446a; the cavity in the bottom portion 400b includes cavity portions 442b, 444b and 446b. As can be seen from FIGS. 12A and 12B, the die 400 can be used as would be understood by those skilled in the art so that cavity portions 442a and 442b form portion 42 of tablet 40, cavity portions 444a and 444b form portion 44 of tablet 40, and cavity portions 446a and 446b form portion 46 of tablet 40.

Figure 13A:
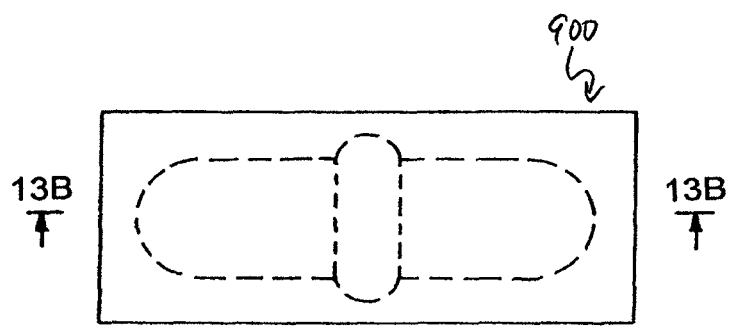
FIG. 13A is a top plan view of one example of a die for forming yet another example of an oral dosage unit of the present invention.
Figure 13B:
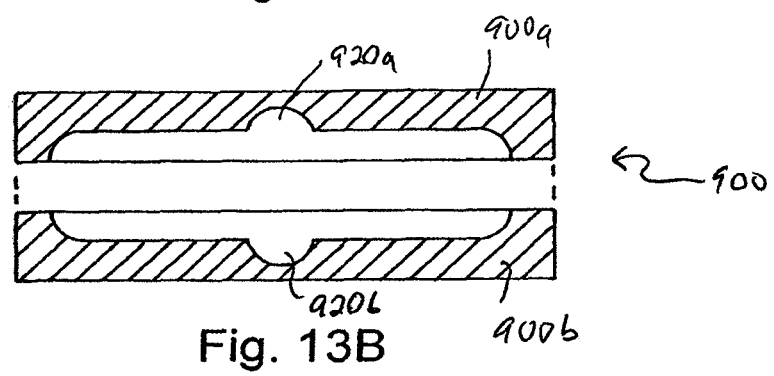
FIG. 13B is a cross-sectional view thereof along line 13B-13B of FIG. 13A.

FIG. 13A is a top plan view of one example of a die for forming yet another example of an oral dosage unit of the present invention and FIG. 13B is a cross-sectional view thereof along line 13B-13B of FIG. 13A. The die 900 has top and bottom die halves 900a, 900b having respective cavities that, in a closed state of the die, correspond to the shape of a tablet of a shape corresponding to tablet 90 shown in, e.g., FIGS. 9A-9C. The cavity is shown in dashed lines in FIG. 13A. The cavity in the top and bottom portions 900a, 900b include respective cavity portions 920a, and 920b. As can be seen from FIGS. 13A and 13B, the die 900 can be used as would be understood by those skilled in the art so that cavity portions 920a and 920b form portion 92 of tablet 90.

Figure 14:
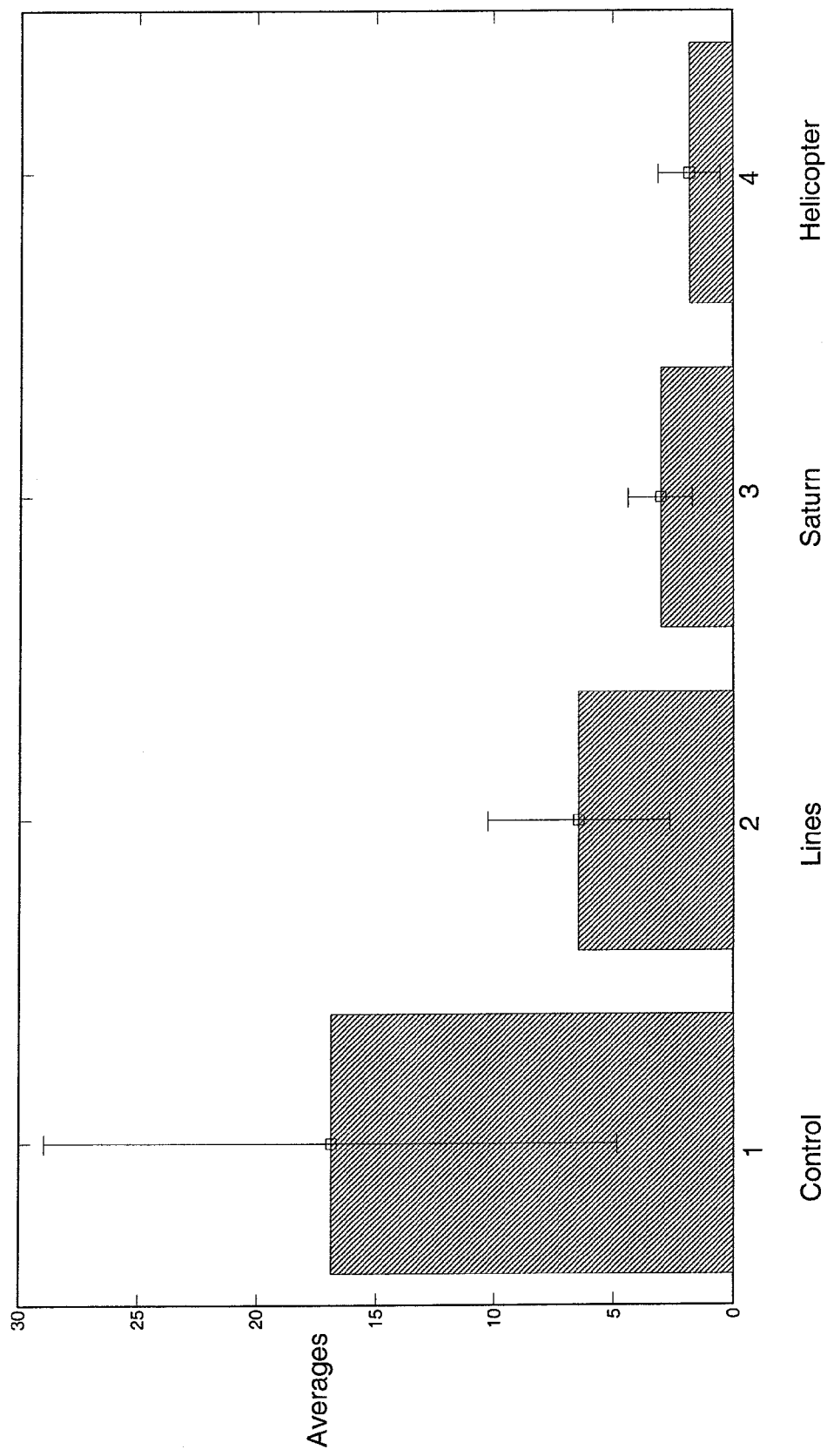
FIG. 14 is graphic representation of the average esophageal transit times (plotted in the vertical access) of four different tablet shapes.

FIG. 14 is graphic representation of the average esophageal transit times (plotted in the vertical access) of four different tablet shapes, Control (a standard oblong pill shape), Lines (modeled on FIG. 5), Saturn (modeled on FIG. 9), and *Helicoptor* (modeled on FIG. 3). The in vivo work yielding these plotted results is described in Example G.

The die shapes shown in FIGS. 11A, 11B, 12A, 12B, 13A and 13B are examples only, and, as would be understood by those skilled in the art, other die shapes can be used to form other examples of the dosage units of the present invention.

As is known to those skilled in the art, two-piece telescoping gelatin or vegetable capsule can be made in two parts by dipping metal rods in the gelling agent solution. In making standard capsule shapes, the rod is merely lifted from the solution and capsule part shed from the metal rod. On the other hand, in making capsules having some of the shapes, e.g., asymmetric shapes, of the present invention (for example the shapes of FIGS. 1A-1C, 2A-2c, 4A-4C, etc.), the capsule part cannot be simply shed from the shaped rod or die, since an end of the shaped rod or die may be wider than the opening of the formed capsule part to be shed. Therefore, contrary to the present state of the art, it would be necessary to use a shaped rod or die the wide portion of which is collapsible so that it the capsule part can be shed therefrom. That is, the die for forming such a dipped capsule around a capsule-forming region thereof includes a region adjacent an end of the capsule forming region that is wider than another portion of the capsule forming region and which can collapse so that the die can shed the formed capsule fragment by removing the die through a neck of the capsule fragment that has a smaller diameter than the width of the region adjacent an end of the capsule forming region.

The following examples demonstrate the advantageous effects of the present invention. However, the present invention is not limited to the following examples or to the embodiments shown in the drawings.

Example A

The following materials were used: Right-Aid brand Ibuprofen gel caps, Scotch brand "Super Strength" packing tape and a slide lock adjustable pliers.

The experiment was fashioned to use the tape as an adhesive surface. The tape was placed at angle thirty three degrees from horizontal include to form an approximately ten inch long ramp. Gel caps—modified and unmodified controls—where placed side by side on the ramp and 20 cc of room temperature water were poured behind the gel caps to determine the ability of the 20 cc of water to dislodge the gel caps from the tape.

The "modified" gel cap was modified by using the pliers on the end of the gel cap so as to render the gel cap pinched (thinner) at the far side. Care was taken to avoid puncture of the gel cap. While a number of gel caps where punctured during practice, after some practice, it became possible to manipulate the end of the gel cap using the pliers without puncture. The "modified" gel cap had a shape similar to that shown in FIGS. 1A-1C.

The result of the pinching was to render the gel cap asymmetric on any rotational axis.

The asymmetric gel cap was placed on the ramp (pinched side downgrade) along side of an unmodified gel cap. The 20 cc of water was then poured behind the two gel caps. The asymmetric gel cap was washed off the tape ramp; the unmodified control remained adhered to the tape ramp without moving.

This experiment was repeated with the pinched side upgrade, again using the unmodified control and 20 cc of water. The result was the same; the asymmetric gel cap was washed off the tape ramp. The unmodified control remained adhered to the tape ramp without moving.

For the purposes of accuracy, each iteration of this experiment was repeated five times—each time with the same results.

It was concluded that the reduction of the contact patch effected by the pinching of the gel cap was responsible for the improved performance of the modified, pinched gel cap over the control.

Example B

It was decided to carry out a different test from that of Example A. In this test, 10 CC of water were placed into a pyrex beaker. The sample tablets were added to a dry pyrex beaker; the water was added and then slowly expelled. The purpose was to see which tablets were expelled with the water (and which were not). A tablet expelled from the beaker was a "pass." A tablet retained in the beaker was a "fail."

The first control (Tablet 1) was a 200 mg Care One Ibuprofen. The second tablet (Tablet 2) was fashioned from modeling clay to mimic the size and shape of Tablet 1, so as to observe any differences caused by the use of modeling clay. The third tablet (Tablet 3) was made by taking tablets like Tablet 2 and pinching one end concave (similar to the shape shown in FIGS. 2A-2C). The second control (Tablet 4) was a 220 mg Aleve Liquid Gel. The fifth tablet (Tablet 5) was made from modeling clay to mimic the size and shape of Tablet 4. The sixth tablet (Tablet 6) was made by taking samples of Tablet 5, and pinching one end (resulting in a concave impression) (similar to the shape shown in FIGS. 2A-2C). The seventh tablet (Tablet 7) was made by pinching both ends (resulting in concave impressions) and then rotating the middle of the tablet by 90 degrees (similar to the shape shown in FIGS. 3A-3C). The third control (Tablet 8) was Good Sense Ibuprofen liquid gels (200 mg).

Five fresh samples of each of the above were used in order to perform five iterations of the experiment with the following results:

| Tablet # | Pass (expelled from beaker) | Fail (retained in beaker) |
|---|---|---|
| Tablet 1 | 0 | 5 |
| Tablet 2 | 1 | 4 |
| Tablet 3 | 4 | 1 |
| Tablet 4 | 0 | 5 |
| Tablet 5 | 1 | 4 |
| Tablet 6 | 5 | 0 |
| Tablet 7 | 5 | 0 |
| Tablet 8 | 0 | 5 |

The slightly improved performance of Tablet 2 over Tablet 1 was attributed to the surface properties—gel caps can be tacky and stick. The reduction of the contact patch size through the use of asymmetric shapes greatly enhanced the propensity of the dosage form to transit.

Example C

The intention of Example C was to re-test crimped soft gels similar to the shape tested in Example A but in this case employing a testing method more similar to that of Example B.

Using an adjustable wrench and Good Sense® 200 mg Ibuprofen Liquid Softgels, we crimped one end of the Softgels to an approximate length of 3/16's of an inch at the crimped end. The testing procedure of Example B was performed approximately thirty minutes after the Softgels were crimped. The results were as follows:

| Unmodified Good Sense ® Liquid Softgel | Crimped Good Sense ® Ligquid Softgel |
|---|---|
| Fail | Pass |
| Fail | Pass |
| Fail | Fail |
| Fail | Pass |
| Fail | Pass |
| Pass | Pass |
| Fail | Fail |
| Implies pass/fail rate of 14.3% | Implies pass/fail rate of 71.4% |

Again, the reduction of the contact patch through the introduction of asymmetry to the shape resulted in an enhanced propensity to transit.

Example D

Example D again uses the methodology of Example B but in this case applied to a modified existing liquid gel that was crimped at both ends and then twisted 90 degrees (similar to the shape shown in FIGS. 4A-4C).

We used Aleve® Liquid Gels (220 mg). Using an adjustable wrench, both ends were crimped. Following crimping of each end, the double crimped Liquid Gel was twisted by 90 degrees.

| Unmodified Aleve ® | Aleve ® with ends crimped and twisted 90 degrees |
|---|---|
| Fail | Pass |
| Fail | Pass |
| Fail | Pass |
| Fail | Pass |
| Fail | Pass |
| 0% Pass rate | 100% pass rate |

This example again demonstrated that the introduction of asymmetry served to increase transit propensity—here in dramatic fashion over the control.

Example E

Again using modeling clay and in some cases a washer (in which the clay was molded around the washer to increase density), sample tablets were made and tested in accordance with the water evacuation method of Example B.

We tested four designs. The first design was initially shaped akin to the Good Sense® 200 mg Ibuprofen tablet. As an added feature to reduce contact surface, ridges were added all around the dosage form, running lengthwise (similar to the shape shown in FIGS. 5A and 5B).

The second design was initially shaped akin to the Aleve® liquid gel. Again, like the previous design, we added ridges running lengthwise to the design (similar to the shape shown in FIGS. 5A and 5B).

The third design was a round disc-shaped tablet built around a washer to increase density. Dimples were created on the two flat sides of this design. The dimples were raised approximately 1-2 mm from the flat portion (similar to the shape shown in FIGS. 6A and 6B).

The fourth design was shaped identically to the third design but it was made solely from clay and thus had a lower density. Again, the dimples were raised approximately 1-2 mm from the flat portion (similar to the shape shown in FIGS. 6A and 6B).

As before, we tested five samples of each design.

|  | Mass of Sample | Pass | Fail |
|---|---|---|---|
| First Design (ridged ibuprofen shape) |  |  |  |
| Sample one | .35 g | Pass |  |
| Sample two | .35 g | Pass |  |
| Sample three | .38 g | Pass |  |
| Sample four | .38 g | Pass |  |
| Sample five | .38 g | Pass |  |
| Second Design (ridged Aleve ® shape) |  |  |  |
| Sample one | .37 g | Pass |  |
| Sample two | .34 g | Pass |  |
| Sample three | .35 g | Pass |  |
| Sample four | .35 g | Pass |  |
| Sample five | .35 g | Pass |  |
| Third Design (weighted dimpled disc) |  |  |  |
| Sample one | .76 g | Pass |  |
| Sample two | .61 g | Pass |  |
| Sample three | .76 g | Pass |  |
| Sample four | .77 g | Pass |  |
| Sample five | .64 g | Pass |  |
| Fourth Design (unweighted dimpled disc) |  |  |  |
| Sample one | .33 | Pass |  |
| Sample two | .36 | Pass |  |
| Sample three | .34 | Pass |  |
| Sample four | .36 | Pass |  |
| Sample five | .34 | Pass |  |

The four designs in this example showed the efficacy of dimples and ridges in reducing surface contact area, thereby reducing adhesion area and promoting effective transit. The absence of any measured difference between designs three and four—of the same design with different densities—created the desire for further study of the role of density in transit.

The embodiments and examples of the invention have been described in detail above, but the invention may include various modifications without departing from the spirit and scope of the invention.

Example F

This example used, as a control, CVS brand 81 mg Aspirin (enteric coated tablets). Each control tablet had a mass of 0.2 grams. Using low density modeling clay, tablets were made in the same shape as the control with a mass of 0.063 grams.

The tablets were tested in a glass container with ¼ cup of room temperature water as follows. The tablet was added to a pre-wetted container. ¼ cup of water was added. The container was immediately inverted. If the sample evacuated, a pass was recorded. If the tablet adhered a fail was recorded. Ten samples of each of the control and low density model were tried with results as follows:

| Number | Control | Low Density Sampole |
|---|---|---|
| 1 | Fail | Pass |
| 2 | Fail | Pass |
| 3 | Fail | Pass |
| 4 | Fail | Pass |
| 5 | Fail | Pass |
| 6 | Fail | Pass |
| 7 | Fail | Pass |
| 8 | Fail | Pass |
| 9 | Fail | Pass |
| 10 | Fail | Pass |

These results suggest that the increased buoyancy associated with lower density tablets enhanced transit—despite the testing method of inverting the beaker (thereby exerting greater gravitational pull on the more dense, control). This suggests a strong benefit to the buoyant sample whereby the increased buoyancy retards the formation of adhesionary forces.

Example G

It was considered valuable to perform in vivo studies of the effect of tablet design on esophageal transit in order to determine the applicability of the in vitro testing described herein. One of the difficulties in this lightly studied area is that there are no established, or even suggested in vitro methods to model transit. Thus, the inventor is left to his own devices.

As concerns in vivo study, however, we are fortunate that study of esophageal transit is understood (see the references cited above).

Four pills were prepared for this study. The excipients included: dibasic calcium phosphate more starch and in the center, a magnetic marker of cylindrical shape: diameter 3 mm and height 4 mm; they were named Control (modeled on tablet 1 of Example B), Lines (modeled on FIG. 5), Saturn (modeled on FIG. 9) and Helicopter (modeled on FIG. 3). Their size was around 20 mm of length and all they have the same weight.

For this study, 21 subjects, males and females, were enrolled: i) age from 17 to 55 years, ii) weight from 52 to 120 kg, iii) height from 1.59 to 1.77 m and iv) body mass index variation from 17.96 to 43.03 kg/m$^2$.

Three magnetic sensors (MS) were used in order to register the pass of each pill through the esophagus: First MS was on the top end of the sternum, next to supra sterna artery; Second MS was 12.5 cm, over the esophagus, from the first one; Third MS was next to Xiphoid process, to 12.5 cm from the second one.

The average esophagus length was 25 cm. This distance was the same for each subject.

SUBJECT POSITION: In semi-Fowler's position, in this case, each patient was lying in bed in a supine position with the head of the bed at 25 degrees.

Data acquisition was performed in LabVIEW platform at rate frequency of 30 samples per second. This file was exported to Matlab platform where it was plotted.

Descriptive statistical was used in order to identify the esophageal transit time.

The Control: mean=16.86, std=12.04 seconds
Variations from minimum to maximum (3.6 to 35.9) seconds.
 The Lines: mean=6.44, std=3.81 seconds
Variations from minimum to maximum (3 to 12) seconds.
 The Saturn: mean=3.04, std=1.35 seconds
Variations from minimum to maximum (1.22 to 4.2) seconds.
 The Helicopter: mean=1.78, std=1.33 seconds
Variations from minimum to maximum (0.3 to 5.17) seconds.

This is an average of a whole each group. These results are graphically shown in FIG. 14.

An average of the whole each group is also shown. In order to see the self variation of each subject was divided in esophageal transit time of his own control, then the descriptive statistical is performed, mean and standard deviations are computed: Control: 100%; Lines: 80%; Saturn: 45%; Helicopter: 18%.

No significant difference was observed by gender, age or weight.

Clear improvements in transit from the control pill to Saturn and Helicopter pills were observed. Some improvement in transit time was observed for the Lines model, even though it is likely that the Lines model was not created with sufficiently deep or properly spaced ridges and valleys so as to further reduce the improvement when compared with the Control. We believe that with modification of the foregoing, the performance of the Lines model would be improved.

This study makes clear that the contact patch reduction does in fact make a substantial clinical difference. These studies, with controls, show consistent objective results that are well beyond any question of effectiveness. Furthermore when an additive feature, such as lowered density/added buoyancy is added to this design, it is obvious that the results would be additive.

By the use of a reduced contact patch, the dosage unit of the present invention makes the esophageal transit of a drug possible regardless of body position. Thus, the present invention allows for the altering of administration instructions for existing medications. For example, with improved transit, the instruction of FOSAMAX® for the patient to remain standing for one hour after administration can be relaxed or even done away with in its entirety.

Two or more of the various embodiments may be combined, with or without a density reduction, to obtain a reduced contact patch. For example, any or all of asymmetry, annular ring, grooves, concavities and convexities may be combined in one dosage unit, with or without a density reduction.

As will be apparent to those skilled in the art, various modifications of the disclosed embodiments and examples can be made without departing from the teachings of the present invention.

What is claimed is:

1. An asymmetric oral dosage unit containing a bioactive at least within the dosage unit selected from the group consisting of a pharmaceutical, biological, antigen, botanical, food, nutraceutical, cosmaceutical and gene therapeutic, the dosage unit having a length along its longitudinal axis longer than a length along all axes perpendicular to the longitudinal axis and being asymmetric with respect to a rotational axis perpendicular to the longitudinal axis of the dosage form, the rotational axis being located substantially at a mid point along the longitudinal axis, the asymmetry being configured to reduce the contact patch of the dosage unit with a flat surface and decrease esophageal transit time when orally administered compared to a dosage unit of the same size but that is symmetric with respect to said rotational axis.

2. The asymmetric oral dosage unit according to claim 1, wherein the dosage unit has opposing end portions along the longitudinal axis, one end portion having a substantially cylindrical shape and an opposite end portion having a flattened area with a thickness smaller than an a radius of the cylindrical portion.

3. The asymmetric oral dosage unit according to claim 2, wherein the opposite end portion having the flattened area with a thickness smaller than and a radius of the cylindrical portion includes a concave depression and/or convex protrusion in at least one surface.

4. The asymmetric oral dosage unit according to claim 1, wherein the dosage unit has opposing flattened end portions along the longitudinal axis having a thickness smaller than a width thereof, wherein the opposing end portions are more than 0° and less than 180° out of phase with respect to the longitudinal axis.

5. The asymmetric oral dosage unit according to claim 4, wherein at least one of the opposing end portions includes a concave depression in at least one surface.

6. The asymmetric oral dosage unit according to claim 4, wherein the dosage unit includes a substantially cylindrical portion at some point along the longitudinal axis.

7. The asymmetric oral dosage unit according to claim 1, wherein an outer surface of the dosage unit is ridged so as to reduce the contact patch of the dosage unit with a flat surface compared to non-ridged dosage unit of the same size and shape.

8. The asymmetric oral dosage unit according to claim 1, wherein the dosage unit has a bulbous shape in which one end is enlarged with respect to another end.

* * * * *